United States Patent
Jones et al.

[19]

[11] Patent Number: 5,963,041
[45] Date of Patent: Oct. 5, 1999

[54] DEVICE AND METHOD FOR TESTING SURGICAL INSTRUMENTS

[75] Inventors: Richard F. Jones, Winnetka, Ill.; Michael Henderson, Indianapolis, Ind.

[73] Assignee: MidiCor Corporation, Vernon Hills, Ill.

[21] Appl. No.: 08/912,521

[22] Filed: Aug. 18, 1997

Related U.S. Application Data

[62] Division of application No. 08/569,722, Dec. 8, 1995, Pat. No. 5,680,053.

[51] Int. Cl.$^6$ .................................................. G01N 27/00
[52] U.S. Cl. ........................... 324/559; 324/536; 324/555; 324/455; 606/34
[58] Field of Search .................................. 324/557, 558, 324/559, 536, 555, 455; 606/32, 34, 35, 41

[56] References Cited

U.S. PATENT DOCUMENTS

| | | | |
|---|---|---|---|
| 1,724,565 | 8/1929 | Dana ........................................ | 324/536 |
| 2,396,172 | 3/1946 | Groven et al. ......................... | 439/476.1 |
| 2,615,077 | 10/1952 | Tinker ..................................... | 324/559 |
| 2,920,270 | 1/1960 | Saw ........................................ | 324/557 |
| 2,979,656 | 4/1961 | Stearns ................................... | 324/559 |
| 3,249,862 | 5/1966 | Mack ...................................... | 324/559 |
| 3,466,537 | 9/1969 | Eigen ...................................... | 324/536 |
| 4,958,128 | 9/1990 | Tomoyasu et al. ..................... | 324/559 |
| 5,084,680 | 1/1992 | Mitchell et al. ........................ | 324/559 |
| 5,302,904 | 4/1994 | Nopper ................................... | 324/536 |
| 5,510,718 | 4/1996 | Enderby ................................. | 324/536 |

FOREIGN PATENT DOCUMENTS 0147059  11/1981  Japan .

*Primary Examiner*—Josie Ballato
*Assistant Examiner*—Thomas Valone
*Attorney, Agent, or Firm*—Olson & Hierl, Ltd.

[57] ABSTRACT

A testing device for detecting defects in insulation of electrosurgical instruments that includes an implement or wand having a distal end, an electrode for generating a spark adapted to detect a defect in the insulation, and mounting means for removably mounting the electrode to the distal end of the implement. The removable mounting means includes a shank that is received in a socket or bore defined in the distal end of the wand and is engageable with the wand within the socket so the shank can easily be removed from the socket after use. The wand is releasably engageable with the housing by a flexible bracket that extends from the housing. The device may include a pad having a reflective top surface with ridges upon which the surgical instrument to be tested is placed.

23 Claims, 3 Drawing Sheets

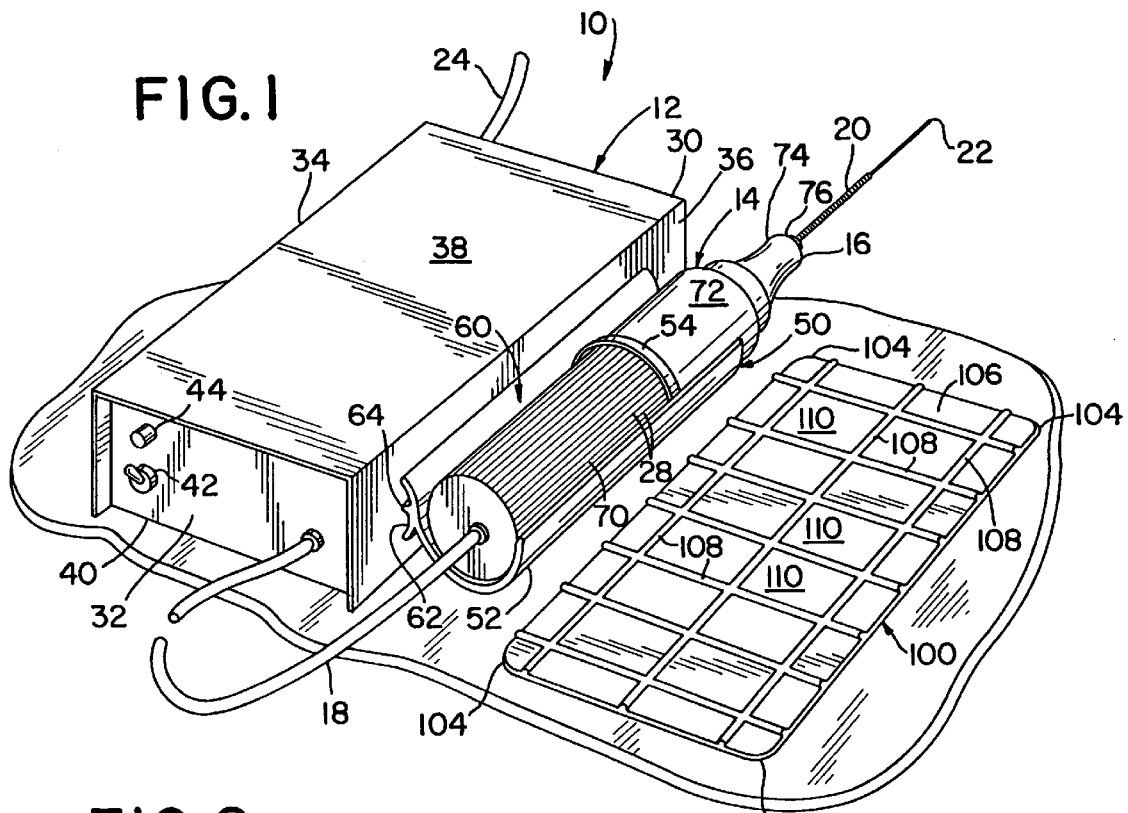

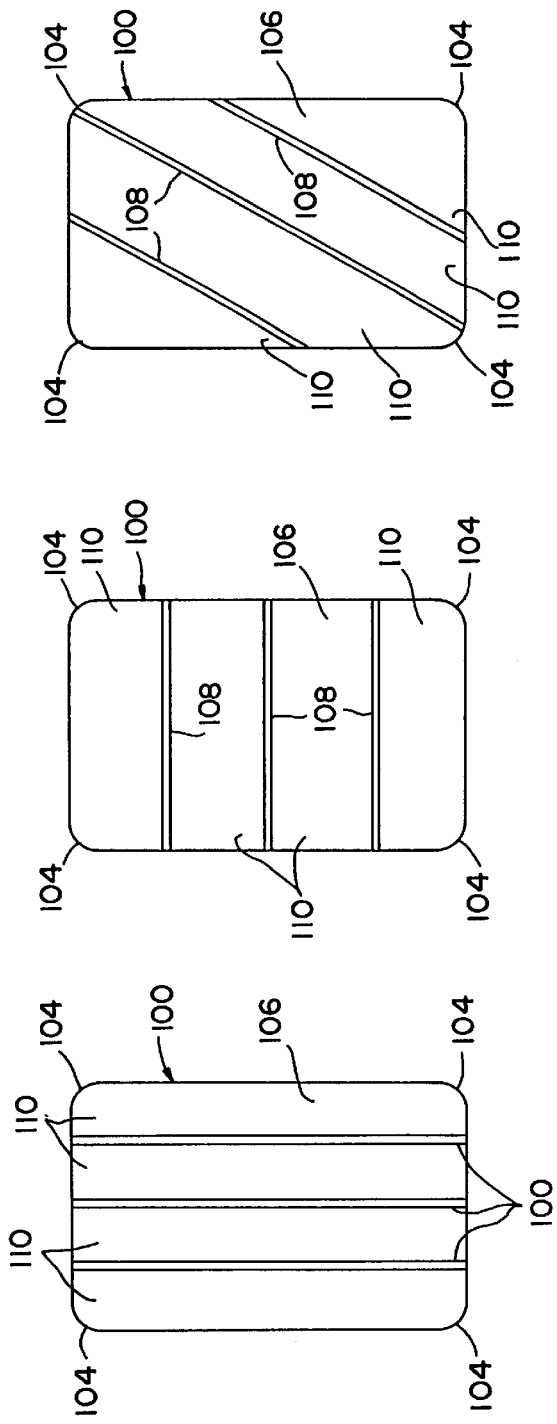

1

DEVICE AND METHOD FOR TESTING SURGICAL INSTRUMENTS

This application is a division of application Ser. No. 08/569,722, filed Dec. 8, 1995 is now U.S. Pat. No. 5,680,053.

TECHNICAL FIELD

The present invention relates to a device and method for testing surgical instruments, and, more particularly, to a device and method for testing insulation of electrosurgical instruments.

BACKGROUND OF THE INVENTION

Since the inception of monopolar and bipolar electrosurgical devices in laparoscopic and other surgery as tools to the surgeon for cutting and coagulating tissue, numerous cases of inadvertent and unwanted electrical shocks and burns to the patient and surgeon have occurred. In a great number of these cases, the cause of the reported injury is believed to be the breakdown of the electrosurgical instrument's insulation, such as holes, cracks or fissures.

Although various types of insulation materials have been utilized, including fluorocarbons, polyvinylchloride (PVC), and heat shrinkable plastic materials, these insulation materials have very little abrasion resistance. In addition, they can be scratched easily, leaving areas with bare metal exposed. They also tend to degrade rapidly with various sterilization methods, causing insulative properties to deteriorate. These defects permit the electricity to jump from the shaft during surgery to untargeted body organs or tissue or to the surgeon, which can cause serious injury to a patient or the surgeon. Ceramic insulation has also been used from time to time; however, porosity and fissures of the ceramic coating can create undesirable electrical pathways.

Accordingly, it is an object of this invention to provide a device and method for testing insulation on electrosurgical instruments that enables medical personnel to quickly and easily test for defects in the insulation.

It is a further object of this invention to provide such a device that includes an electrode adapted to be energized to produce a high voltage, high frequency spark for detecting the defect, and, preferably, to provide such an electrode that is removable to enable fast and easy treatment or replacement of the electrode.

It is a further object of this invention to provide a dielectric testing pad to be used with such a device to facilitate the test procedure.

SUMMARY OF THE INVENTION

A testing device is provided for testing insulation of electrosurgical instruments such as those used in laparotomy that enables medical personnel to quickly and accurately detect defects, such as holes, cracks or fissures, in the insulation. In a preferred embodiment, the device includes an elongated implement having a distal end, a flexible electrode mounted to the distal end, operably associated with energizing circuitry contained within a housing, and adapted to be energized so as to produce a spark, and a mounting socket at the distal end for removably receiving the flexible electrode in the distal end of the implement.

The flexible electrode includes a shank that is received in the mounting socket or bore defined in the distal end of the implement. The shank is engageable within the socket in any suitable manner, such as by a frictional engagement, so the shank can easily be removed from the socket after use. If desired, a grip may be provided to the shank to facilitate removal of the electrode for sterilization.

The device may also include a retaining clamp for removably engaging the implement. The clamp can be a flexible bracket extending from the housing. In the preferred embodiment, the implement is generally cylindrical along most of its length, and the bracket is defined by an arcuate wall having a generally semicircular cross section to complement the configuration of the implement. The implement may include an annular boss or band that engages the bracket by a pressure fit.

A dielectric pad is provided upon which a surgical instrument may be placed during testing. The pad preferably is rectangular with rounded corners, and has a gridded top surface that is defined by a plurality of ridges. During testing, the surgical instrument is supported by the ridges at an elevated height to decrease the surface area of the instrument that is in contact with the top surface, and, thus, increase the exposed surface area of the insulation on which a defect can be detected. Desirably, the top surface is reflective to increase the surface area of the surgical instrument that can be viewed during testing.

With the present invention, insulated electrosurgical instruments may be tested for defects quickly and easily. If the dielectric pad is used, the electrosurgical instrument is first positioned on the pad. The electrode is then energized to generate, at a frequency preferably in the range of about 3 to 4 megahertz, a voltage of at least about 35,000 volts, and desirably about 40,000 volts, at a tip of the electrode so as to produce a high voltage, high frequency spark. The electrode is then moved along the insulated surface of the electrosurgical instrument to detect defects that manifest themselves by localizing the distal end of the spark as the electrode is moved along the instrument to be tested.

Accordingly, a testing device and method are provided for testing insulation on surgical instruments that enables medical personnel to quickly and accurately detect defects in the insulation that, if left undetected, could cause serious injury to a surgical patient or possibly the surgeon. The testing device is compact, convenient and simple to use. Because the electrode is removably mounted to the implement, it can be quickly and easily sterilized by autoclaving or replaced during repeated use. The testing device is easy to transport and work with because the implement is removably engageable with the housing. The dielectric pad, with its gridded and reflective top surface, further enhances the performance of the device.

BRIEF DESCRIPTION OF THE DRAWINGS

The present invention and the advantages thereof will become more apparent upon consideration of the following detailed description when taken in conjunction with the accompanying drawings.

FIG. 1 is a perspective view of an insulation testing device in accordance with a preferred embodiment of the invention;

FIG. 2 is a plan view of the removable electrode of the insulation testing device of FIG. 1 together with a mount therefor, in the form of a grip and a shank, for removably securing the electrode to the implement;

FIG. 3 is a broken plan view of the implement of FIG. 1 and the electrode removably mounted to the implement, illustrating with dashed lines the electrode shank received within a socket defined in the implement;

FIG. 4 is a partial operational view of the insulation testing device of FIG. 1, showing an electrosurgical instru- FIG. 5 is an alternative embodiment of the top surface of the testing pad of FIG. 1 having ridges that extend in the longitudinal direction of the testing pad;

FIG. 6 is another alternative embodiment of the top surface of the testing pad of FIG. 1 having ridges that extend in the lateral direction of the testing pad;

FIG. 7 is yet another alternative embodiment of the top surface of the testing pad of FIG. 1 having ridges that extend diagonally along the testing pad;

FIG. 8 is a circuit diagram of a Tesla coil that can be employed as energizing circuitry to produce the high voltage, high frequency spark at the tip of the electrode.

DETAILED DESCRIPTION OF PREFERRED EMBODIMENTS

Figure 9:
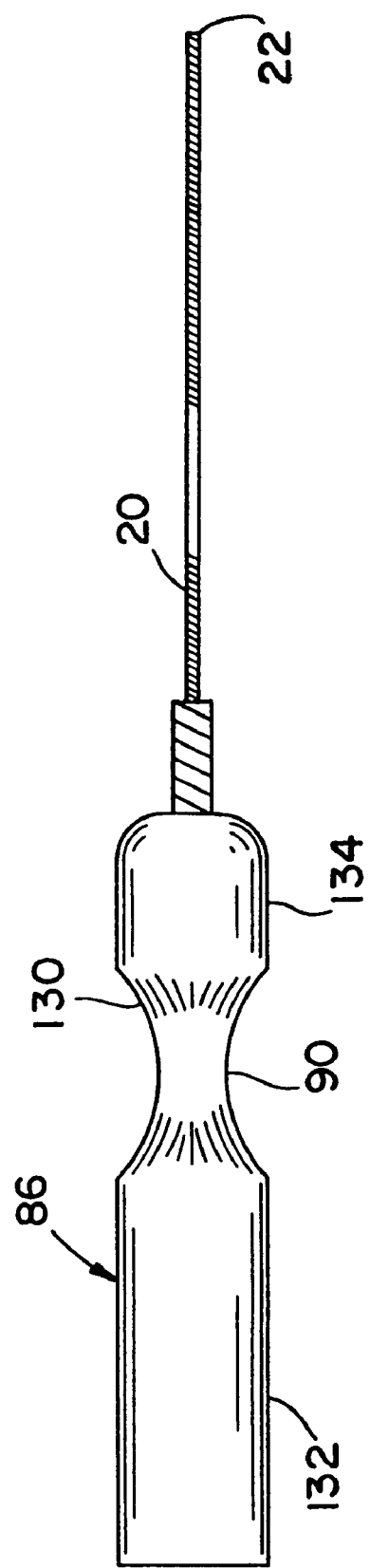
FIG. 9 is a plan view of another embodiment of the removable electrode for the insulation testing device of FIG. 1 illustrating an alternative embodiment of the mount.

Referring to FIG. 1, a testing device 10 is provided for testing of insulated electrosurgical instruments such as those used in laparotomy to detect defects, such as holes, cracks or fissures, in the insulation of such instruments. In a preferred embodiment, the device 10 includes a housing 12 for energizing circuitry, an implement or wand 14 that is generally cylindrical along most of its length and has a distal end 16, a cable 18 of suitable length electrically connecting the housing to the wand, and an electrode 20 operably associated with the energizing circuitry and removably mounted to the distal end of the implement or wand 14.

Circuitry included in the housing 12 is adapted to receive power input from a power source and to generate a relatively high voltage in a tip 22 of the electrode 20 to produce a high voltage, high frequency spark that extends from the tip. Any circuitry capable of achieving the spark can be employed. A conventional Tesla coil (see FIG. 8), for example, can be used as the energizing circuitry.

In a preferred embodiment, the voltage generated is at least about 35,000 volts, and desirably about 40,000 volts. The voltage is generated at a frequency in the range of about 3 to 4 megahertz. The circuitry may be energized by any suitable voltage, such as, for example, at 115 or 230 volts at 50/60 hertz.

Power is usually supplied to the electrode energizing circuitry through a polarized and grounded power cord 24 that extends from the housing 12 to any suitable power source such as a three wire electric socket.

The housing 12 preferably is generally rectangular and box-shaped, and includes front and rear panels 30, 32, two side panels 34, 36, and top and bottom panels 38, 40, all of which are generally rectangular. A power switch 42 for energizing the circuitry and an indicator light 44 that illuminates when the circuitry is energized may be included on the rear panel 32. The housing 12 may include a fuse (not shown), such as, for example, a 1 Ampere fuse. The fuse may be secured within the housing 12 or to this outside of the housing. The power cord 24 is illustrated as extending from the front panel 30 of the housing 12.

In a preferred embodiment, the housing 12 includes a flexible bracket 50 for receiving and releasably engaging the implement or wand 14 when it is not in use. The bracket 50 is defined by an arcuate, generally semicircular wall 52 that extends from and along one of the side panels 36 and complements the generally cylindrical shape of the implement or wand 14. The bracket may be constructed of any suitable material, such as a plastic or metal.

Desirably, the implement or wand 14 includes an annular boss or band 54 to facilitate a pressure fit retaining engagement with the bracket 50. The annular boss 54 has an outer diameter that is slightly larger than the inner diameter of the bracket 50 when the bracket is in its unflexed state. When the implement or wand 14 is pressed into the bracket 50, the bracket flexes to accommodate the annular boss 54.

The bracket 50 may be secured to the housing 12 in any suitable manner. In the illustrated embodiment, for example, an arcuate brace 60 is provided that includes on its underside 62 an integral support panel 64 that extends along the length of the brace 60. The support panel 64 is secured to the side panel 36 of the housing 12 in any suitable manner such as by a plurality of fasteners or an adhesive.

Desirably, the implement or wand 14 includes a handle portion 70 and a distal portion 72 that are separated by the boss 54. In the illustrated embodiment, the boss 54 is located roughly halfway along the length of the implement or wand 14. A plurality of ridges 28 extend longitudinally along the handle portion 70 to provide a convenient grip for the personnel using the test device. The distal portion 72 of the implement or wand 14 includes a tapered portion 74 that terminates in a front face 76. The implement or wand 14 may be constructed of any suitable material having high insulative properties, such as, for example, a plastic material.

In the preferred embodiment, the electrode 20 comprises a wire that is coiled along most (see FIGS. 1–4) or at least some (see FIG. 9) of its length to impart flexibility to the electrode, extends linearly in the distal direction along the rest of its length, and terminates at its distal end in the tip 22. The electrode 20 may be removably mounted to the implement or wand 14 in any suitable manner. For example, a cylindrical socket or bore 82 may be defined in the implement or wand 14 at the front face 76 by an inner cylindrical wall 84 extending proximal of the front face. The electrode 20 is mounted to a cylindrical shank 86 that is removably received in the socket 82, and is frictionally engageable with the inner wall 84 so the shank can be removed readily from the socket after use (see FIGS. 2 and 3) for purposes of sterilization or replacement. Alternatively, the shank 86 and inner wall 84 may be engageable by threads (not shown) defined on the shank and inner wall.

If desired, the electrode 20 may be provided with a grip 90 on shank 86 for facilitating removal of the electrode. In the preferred embodiment, the grip 90 includes a cylindrical portion or knob 92 and a conical portion 94. When the shank 86 is received within the socket 82 of the implement or wand 14, the cylindrical portion 92 abuts the front face 76 of the wand, and the conical portion 94 extends distally of the cylindrical portion. The shank 86 can be removed from the socket 82 by grasping and pulling or twisting the grip 90. If desired, the cylindrical portion 92 may be knurled or ribbed for gripping purposes.

Alternatively, as shown in FIG. 9, the grip 90 may be in the form of an annular groove 130 defined on the shank 86 for receiving the fingers of the personnel. With this embodiment, the shank 86 defines a proximal portion 132 that is removably received in the socket 82 and a distal portion 134 that carries the electrode. The groove 130 extends between the proximal and distal portions 132, 134. When the proximal portion 132 of the shank 86 is received within the socket 82, the groove 130 and the distal portion 134 of the shank are outside the socket 82 so that the shank can be readily removed by the personnel by grasping the shank within the groove.

In the preferred embodiment, the testing device includes a dielectric pad 100 upon which an electrosurgical instrument 102 to be tested is placed (see, e.g., FIGS. 1 and 4–7). The dielectric pad 100 preferably is generally rectangular with rounded corners 104, and includes a gridded top surface 106 having a plurality of ridges 108. The electrosurgical instrument 102 is supported elevated by the ridges 108 during testing to decrease the surface area of the electrosurgical instrument that is in contact with the pad 100 and to increase the exposed surface area of the electrosurgical instrument available for visual inspection and monitoring. Thus, the ridges provide additional surface area of insulation that can be exposed to the spark generated by the test device. In addition, the ridges define a plurality of voids or cavities 110 that provide an area in which any residual fluids can collect without interfering with the test. Desirably, the top surface 106 of the pad 100 is reflective to increase the surface area of the electrosurgical instrument 102 that the personnel performing the test can view during testing.

The height of the ridges 108 relative to the bottom of the cavities 110 preferably is in the range of about 1/32 inch to 1/2 inch. The desired arrangement of the ridges 108 may depend upon the configuration of the surgical instrument being tested. The ridges 108 may, for example, extend longitudinally (see FIG. 5) laterally (see FIG. 6) or both (see FIG. 1). Instead (or additionally), the ridges 108 may extend diagonally across the pad (see FIG. 7).

The pad 100 is constructed of a material that can withstand exposure to the voltage generated at the electrode tip for the time period necessary to test the surgical instrument. Desirably, the material is able to withstand about 40,000 volts for a period of 15 seconds without deformation or degradation of the material. The material also should be able to withstand any necessary treatment such as autoclaving and sterilization, and preferably is fully dense to reduce the possibility that bacteria can develop in the pad. The dielectric strength of the material preferably is at least about 400 volts/mil, and the dielectric constant at 1 MHz is no more than about 3.5. The dielectric pad 100 may be constructed of acrylonitrile-butadiene-styrene (ABS; dielectric strength: 425 volts/mil; dielectric constant at 1 MHz:2.6), polycarbonate (dielectric strength: 425 volts/mil; dielectric constant at 1 MHz:3.1); polyetherimide (dielectric strength: 800 volts/mil; dielectric constant at 1 MHz:3.2), or like materials having similar dielectric properties. Desirably, the top surface 106 is coated with acrylic resin to provide a reflective surface.

The dimensions of the dielectric pad 100 may be tailored to the typical length of the surgical instruments to be tested. Desirably, the thickness of the pad 100 is in the range of about 1/32 inch (about 0.8 mm) to about 3/4 inch (about 19 mm) to minimize warping.

The device 10 may be used to test any suitable electrosurgical instrument such as, for example, the electrosurgical instrument 102 illustrated in FIG. 4, which comprises a hollow elongate tube 122 having a working element 124 at its distal end. Insulation 126 comprised of high dielectric material extends along the tube from adjacent its distal end to adjacent its proximal end, and substantially encloses the tube along the length of the tube.

Because of its design, the device 10 may easily be hand carried to the location where the electrosurgical instrument 102 is to be tested. Thereafter, the electrosurgical instrument 102 may be positioned on the pad 100, which includes the reflective top surface 106 and ridges 108 to enhance the performance of the device 10.

After the power cord 24 is inserted into the electric socket, the implement or wand 14 is disengaged from the bracket 50 and positioned so that the tip 22 of the electrode 20 is adjacent (preferably within one inch) or touches the surface of the insulation 126 of the electrosurgical instrument 102 adjacent one end of the insulation. The power switch 42 is switched to the "on" position, thereby generating at a frequency in the range of about 3 to 4 megahertz a voltage of preferably about 40,000 volts at the tip 22 of the electrode 20 so that the electrode produces a spark at its tip.

The tip 22 of the electrode 20 is then moved slowly along the surface of the insulation 126 of the electrosurgical instrument 102, preferably covering the entire length of the insulation of the instrument. Any defect in the insulation 126, such as holes, cracks or fissures, will be indicated by a bright concentration of the spark which extends from the tip 22 of the electrode 20 through the defect to the conductive material of the instrument 102. An illustration of a defect 200 being detected is provided in FIG. 4.

If no defects are found, the instrument 102 is turned over, and the tip 22 of the electrode 20 again is moved slowly along the surface of the insulation 126 of the instrument. Preferably, the testing time for each side should not exceed five seconds. If a defect is detected in the insulation, the instrument should be removed from service until repaired.

After testing is completed, the power switch 42 should be switched to the "off" position, and the electrode 20 is removed from the implement or wand 14 by pulling or twisting the grip 90. The electrode 20 can then be treated (e.g., sterilized by autoclaving, etc.) and remounted on the implement or wand 14, or a new electrode can be mounted thereto. The implement or wand 14 is then secured within the bracket 50, the power cord 24 is disengaged from the power source, and the housing 12 can be hand carried to another location for other testing or for storage.

At any time the device 10 can be tested to determine whether it is operable. With the power switch 42 in the "on" position, the tip 22 of the electrode 20 can be brought to within one inch of the housing 12, which preferably is comprised of a metal casing. If the device 10 is operable, a spark having an arc a minimum of 1/2 inch (10 mm) in length will be generated from the tip 22 of the electrode 20. If the arc produced is less than this, the device needs to be serviced.

The foregoing description is for purposes of illustration only and is not intended to limit the scope of protection accorded this invention. The scope of protection is to be measured by the following claims, which should be interpreted as broadly as the inventive contribution permits.

What is claimed is:

1. A device for testing insulated electrosurgical instruments to detect defects in the insulation of the instruments, the device including:

(a) an implement having a distal end;
   (b) an elongated wire electrode terminating in a tip, removably mounted to the distal end of the implement, and adapted to be energized by high voltage so as to produce a spark that extends from the electrode, the spark adapted to detect a defect in the insulation of an insulated electrosurgical instrument by passing through the defect to a conductive material of the instrument when the electrode is adjacent the defect; and
   (c) arcuate mounting means for removably mounting the electrode to the distal end of the implement.

2. The device of claim 1 wherein the implement defines a socket at its distal end and the mounting means includes a shank mounted to an end of the electrode, at least a portion of the shank being complementary to and receivable within the socket.

3. The device of claim 2 wherein said portion of the shank and the socket are generally cylindrical.

4. The device of claim 2 wherein the socket is defined by an inner wall and said portion of the shank and the inner wall are frictionally engageable.

5. The device of claim 2 further including a grip mounted to said end of the electrode to facilitate removal of said portion of the shank from the socket.

6. The device of claim 5 wherein the grip is a knob.

7. The device of claim 5 wherein the grip is in the form of a groove defined by the shank.

8. The device of claim 6 wherein the shank has a circular cross section substantially along its length and the groove is defined annularly around the shank.

9. The device of claim 1 including a dielectric pad having a top surface upon which the electrosurgical instrument is placed during testing.

10. The device of claim 9 wherein the top surface is reflective to enhance viewing the electrosurgical instrument.

11. The device of claim 9 wherein a plurality of ridges are defined on the top surface for supporting the electrosurgical instrument and reducing the surface area of the electrosurgical instrument that is in contact with the top surface.

12. The device of claim 11 wherein the pad is generally rectangular and at least some of the ridges extend in the longitudinal direction of the pad.

13. The device of claim 11 wherein the pad is generally rectangular and at least some of the ridges extend in the lateral direction of the pad.

14. The device of claim 11 wherein the pad is generally rectangular and some of the ridges extend in the longitudinal direction of the pad and at least some of the other ridges extend in the lateral direction of the pad.

15. The device of claim 11 wherein the pad is generally rectangular and at least some of the ridges extend diagonally.

16. A device for testing insulated electrosurgical instruments to detect defects in the insulation of the instruments, the device including:

(a) an implement having a distal end;

(b) an elongated wire electrode terminating in a tip and removably mounted to the distal end of the implement;

(c) a housing including high voltage energizing circuitry electrically connected to the electrode for energizing the electrode so as to produce a spark that extends from the electrode, the spark adapted to detect a defect in the insulation of an insulated electrosurgical instrument when the electrode is adjacent the defect by passing through the defect to a conductive material of the instrument; and (d) arcuate means for removably engaging the implement and the housing.

17. The device of claim 16 wherein the engaging means includes a flexible bracket extending from the housing for receiving the implement.

18. The device of claim 17 wherein the implement is generally cylindrical along most of its length and the bracket is defined by an arcuate wall having a generally semi-circular cross section.

19. The device of claim 17 wherein the housing includes a pair of side panels, the bracket secured to one of the side panels and extending along said one side panel.

20. The device of claim 19 wherein the housing is generally box shaped and includes a rectangular top panel and a rectangular bottom panel.

21. The device of claim 18 wherein a boss is defined on the implement, the bracket adapted to engage the boss by a pressure fit.

22. The device of claim 21 wherein the boss extends annularly around the implement.

23. The device of claim 16 wherein the implement includes a handle portion having ridges to provide a better grip for a user of the device.

* * * * *

UNITED STATES PATENT AND TRADEMARK OFFICE
CERTIFICATE OF CORRECTION

PATENT NO. : 5,963,041
DATED : October 5, 1999
INVENTOR(S) : Richard F. Jones et al.

It is certified that error appears in the above-indentified patent and that said Letters Patent is hereby corrected as shown below:

Title Page, Section "[73] Assignee:", "MidiCor" should be -- MediCor --, i.e., the Assignee should read as follows: MediCor Corporation.

Col. 3, line 61, "this" should be -- the --.

Signed and Sealed this

Ninth Day of May, 2000

Attest:

Q. TODD DICKINSON

*Attesting Officer*  *Director of Patents and Trademarks*